United States Patent [19]
Antranikian et al.

[11] Patent Number: 5,486,469
[45] Date of Patent: Jan. 23, 1996

[54] THERMOSTABLE FERVIDOBACTERIUM PULLULANASES

[75] Inventors: Garabed Antranikian, Seevetal, Germany; Per L. Jorgensen, Copenhagen, Denmark

[73] Assignee: Novo Nordisk A/S, Bagsvaerd, Denmark

[21] Appl. No.: 94,204

[22] PCT Filed: Mar. 13, 1992

[86] PCT No.: PCT/DK92/00079

§ 371 Date: Aug. 3, 1993

§ 102(e) Date: Aug. 3, 1993

[87] PCT Pub. No.: WO92/16617

PCT Pub. Date: Oct. 1, 1992

[30] Foreign Application Priority Data

Mar. 15, 1991 [DK] Denmark ................................ 472/91

[51] Int. Cl.⁶ .......................... C12N 9/44; C12N 15/56; C12N 15/70; C12N 15/74
[52] U.S. Cl. .................. 435/210; 435/200; 435/691; 435/252.3; 435/252.31; 435/252.33; 435/320.1; 536/23.2; 935/14; 935/29; 935/73; 935/74
[58] Field of Search .................... 435/200, 210, 435/211, 69.1, 252.3, 252.31, 252.33, 320.1, 98, 105; 536/23.2

[56] References Cited

U.S. PATENT DOCUMENTS

| | | | |
|---|---|---|---|
| 4,469,791 | 9/1984 | Colson et al. | 435/252.31 |
| 4,612,287 | 9/1986 | Coleman et al. | 435/172.3 |
| 4,628,028 | 12/1986 | Katkocin et al. | 435/95 |
| 4,628,031 | 12/1986 | Zeikus et al. | 435/205 |
| 4,657,865 | 4/1987 | Takasaki | 435/202 |
| 4,814,267 | 3/1989 | Zeikus et al. | 435/95 |
| 4,929,557 | 5/1990 | Antranikian et al. | 435/202 |
| 4,946,789 | 8/1990 | Udaka et al. | 435/252.3 |
| 4,971,723 | 11/1990 | Chiu | 252/315.3 |
| 5,055,403 | 10/1991 | Tominura | 435/210 |

FOREIGN PATENT DOCUMENTS

| | | |
|---|---|---|
| 0063909 | 11/1982 | European Pat. Off. . |
| 0258050 | 3/1988 | European Pat. Off. . |
| 0276806 | 8/1988 | European Pat. Off. . |
| 0402092 | 12/1990 | European Pat. Off. ............. 435/210 |
| 2023872 | 1/1990 | Japan ................................ 435/210 |

OTHER PUBLICATIONS

R. Huber et al., Arch Microbiol., vol. 154, pp. 105–111, 1990.
B. K. C. Patel et al., System. Appl. Microbiol., vol. 8, pp. 128–136, 1986.
A. R. Plant et al., System. Appl. Microbiol., vol. 9, pp. 158–162, 1987.
D. G. Pitcher et al., Letters in Applied Microbiology, vol. 8, pp. 151–156 (1989).
Sashihara, N., et al., 1988, FFMS Microbiology Letters, 49(3):385–388.
Odibo, F. J. C., et al., (1988, Journal of Industrial Microbiology, 3(6):343–350.
Brown, S. H., et al., 1990, Applied and Environmental Microbiology 56(7):1985–1991.
Kunki, T., et al., 1990, Journal of Fermentation and Bioengineering, 69(4):204–210.
Patel, B. K. C., et al., 1985, Archives of Microbiology, 141(1):63–69, Antranikian, G., 1989, Applied Biochemistry

(List continued on next page.)

Primary Examiner—Robert A. Wax
Assistant Examiner—William W. Moore
Attorney, Agent, or Firm—Steve T. Zelson; Elias J. Lambiris

[57] ABSTRACT

The invention relates to thermostable pullulanases endogenous to the strain *Fervidobacterium sp.* Ven 5, DSM 6204, or a mutant thereof which is capable of producing the pullulanase having (a) a temperature optimum in the range 80–90° C.; (b) a pH optimum in the range of 5–7; and (c) at least 60% residual activity after 24 hours of incubation at pH 6.0. The invention also relates to the use of the pullulanases in starch converting processes, and to saccharification processes.

8 Claims, 7 Drawing Sheets

U.S. PATENT DOCUMENTS and Biotechnology, 20/21:267–279.

Saha, B. L., et al., 1988, The Biochemical Journal, 252(2):343–348.

Kimura, T., et al., 1990, Applied Microbiology and Biotechnology, 34(1):52–56.

Burchhardt, G., et al., 1991, Current Microbiology, 22(1):91–95.

Saha, B. L., et al., 1989, Trends in Biotechnology, 7:234–239.

Kristjansson, J. K., 1989, Trends in Biotechnology 7:349–353.

1 hour　　　2 hours　　　4 hours 6 hours　　　24 hours　　　48 hours

Fig. 6

1 hour     2 hours     4 hours 6 hours     24 hours     48 hours

Fig. 7

THERMOSTABLE FERVIDOBACTERIUM PULLULANASES

TECHNICAL FIELD

This invention relates to thermostable enzymes. More specifically, the invention relates to novel thermostable pullulanases obtainable from Thermotogales, and to processes for the preparation of these enzymes.

The invention also relates to the use of the pullulanases in starch converting processes, and to saccharification processes.

BACKGROUND ART

Thermostable pullulanases are known and have been isolated from e.g. *Bacillus acidopullulyticus*, and their use in industrial saccharification processes has been described, vide EP patent publication No. 63,909. To comply with the demands for more thermostable enzymes, the search has continued, and it is the purpose of this invention to provide novel pullulanases with improved thermostability.

STATEMENT OF THE INVENTION

We have isolated a microorganism producing a novel pullulanase of surprising thermostability.

Accordingly, the invention provides a pullulanase having temperature optimum in the range 80–90° C., pH optimum in the range of 5–7, at least 60% residual activity, preferably at least 80% residual activity, after 24 hours of incubation at pH 6.0, and having immunochemical properties identical or partially identical to those of the pullulanases derived from the strain Fervidobacterium sp. Ven 5, DSM 6204.

In another aspect, the invention provides a process for the preparation of a pullulanase, which process comprises cultivation of a pullulanase producing strain of Thermotogales under anaerobic conditions in a suitable nutrient medium, containing carbon and nitrogen sources and inorganic salts, followed by recovery of the desired enzyme.

In yet another aspect, the invention provides a process for the preparation of a recombinant pullulanase, the process comprising isolating a DNA fragment encoding the pullulanase, combining the DNA fragment with an appropriate expression signal in an appropriate plasmid vector, introducing the plasmid vector into an appropriate host either as an autonomously replicating plasmid or integrated into the chromosome, cultivating the host organism under aerobic conditions in a suitable nutrient medium, leading to expression of the pullulanase and recovering the pullulanase from the culture medium.

In a further aspect, the invention relates to the use of these pullulanases for the saccharification of liquefied starch, and the invention provides a process for converting starch into syrups containing glucose and/or maltose, which process comprises conducting the saccharification of starch hydrolysates in the presence of a pullulanase and one or more enzymes selected from the group consisting of glucoamylase, α-glucosidase, β-amylase, or other saccharifying enzymes.

BRIEF DESCRIPTION OF DRAWINGS

The present invention is further illustrated by reference to the accompanying drawings, in which:

FIG. 2 shows the analysis of sugars released by the action of the pullulanase of the invention during degradation of pullulan (FIG. 2A), branched oligosaccharides (FIG. 2B), and amylose (FIG. 2C), respectively. Left side without pullulanase, right side after 8 hours of incubation at 80° C. 0.25 U/ml was used throughout incubation;

FIG. 3 shows thermal stability of the pullulanase at 70° C. (■), 80° C. (♦), and 90° C. (□) at pH 6.0 in the absence of starch and metal ions (3A, 0–24 hours; 3B, 0–1 hour). Initial activity of the pullulanase solution used for the investigation of thermal stability was 6.5 U/ml;

FIG. 4 shows thermal stability of the pullulanase at pH 45 and 80° C. in the presence of 5 mM $CaCl_2$ (♦), 1% starch (■), 5 mM $CaCl_2$ and 1% starch (◇), and without metal ions or starch (□) (4A, 0–48 hours; 4B, 0–1 hour). Initial activity of the pullulanase solution used for the investigation of thermal stability was 6.5 U/ml;

DETAILED DESCRIPTION OF THE INVENTION

The Enzyme

The present invention provides novel pullulytic enzymes obtainable from an anaerobic microorganism of Thermotogales, preferably a strain of the genus Fervidobacterium, most preferred the strain Fervidobacterium sp. Ven 5 (depositor's reference), or a mutant or a variant thereof. The pullulytic enzymes of the invention have immunochemical properties identical or partially identical to those of a pullulanase obtainable from the strain Fervidobacterium sp. Ven 5.

The strain Fervidobacterium sp. Ven 5 has been deposited by the inventors for patent purposes according to the Budapest Treaty at Deutsche Sammlung von Mikroorganismen on 25 Apr. 1990, under deposit No. DSM 6204.

By an enzyme variant or mutated enzyme is meant an enzyme obtainable by alteration of the DNA nucleotide sequence of the parent gene or its derivatives. The enzyme variant or mutated enzyme may be expressed and produced when the DNA nucleotide sequence encoding the enzyme is inserted into a suitable vector in a suitable host organism. The host organism is not necessarily identical to the organism from which the parent gene originated. The enzyme variant or mutated enzyme is understood as being functionally equivalent to the parent enzyme.

The enzymes of the invention are valuable for use in starch converting processes in combination with other enzymes for industrial conversion of starch into various sugars.

The pullulytic enzymes of the invention can be described by the following characteristics.

Physical-chemical Properties

Figure 1A:
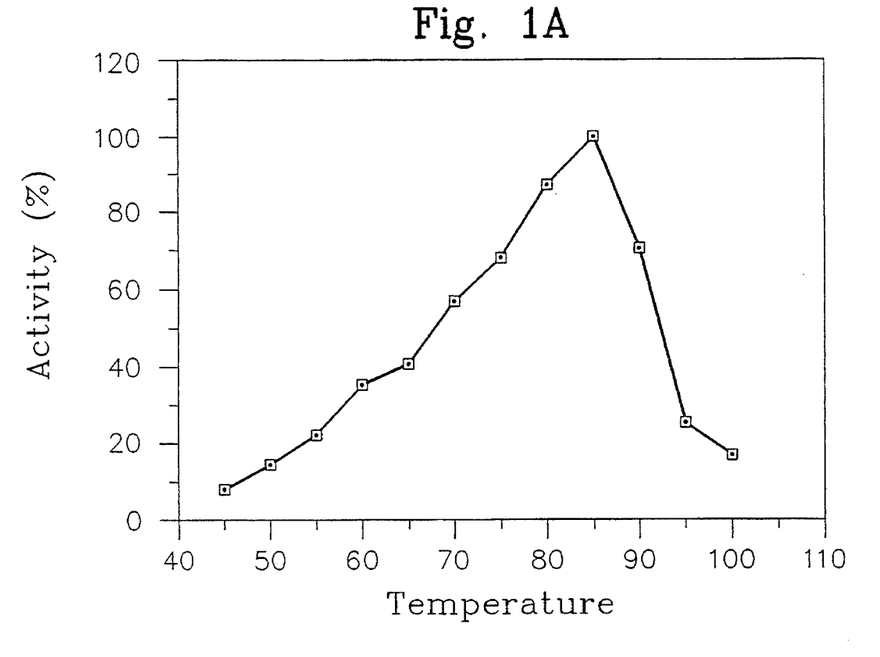
FIG. 1A shows the relative activity (%) of the pullulanase of the invention at different temperatures; 1.2 U/ml were used in incubation for the determination of temperature optimum.

The pullulanase is active at temperatures from below 45° C. to above 100° C., having its temperature optimum in the range of from 75°–90° C., more preferred in the range 80°–90° C., around 85° C., as shown in FIG. 1A.

Figure 1B:
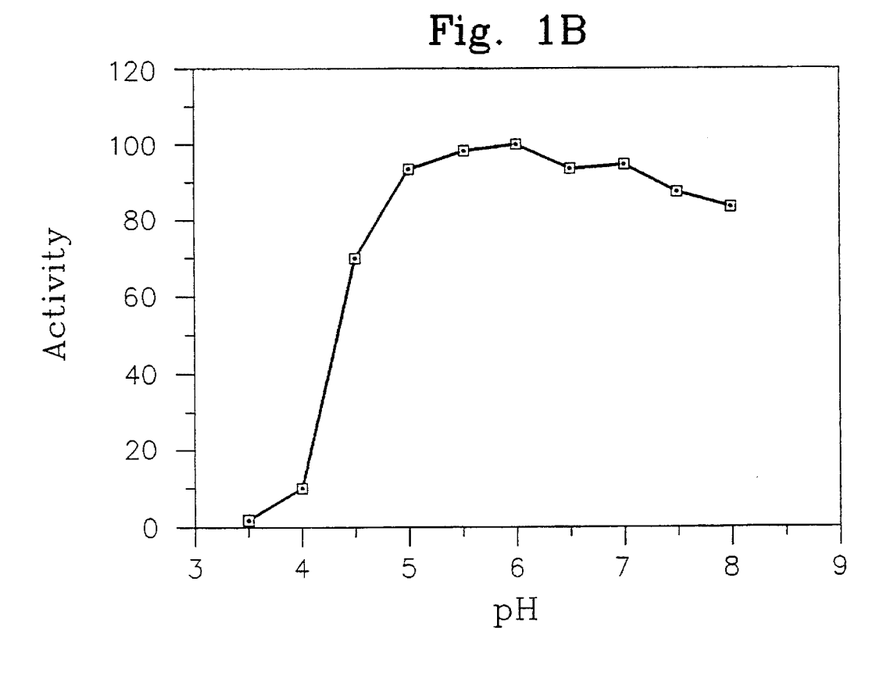
FIG. 1B shows the relative activity (%) of the pullulanase of the invention at different pH values; 1.8 U/ml were used throughout for pH optimum determination.

The pullulanase is active of from pH approx. 3.5 to pH above 8, having a rather broad pH optimum in the range of from ph 4.5 to pH above 8, more preferred in the range pH 5–7, as shown in FIG. 1B.

Figure 3A:
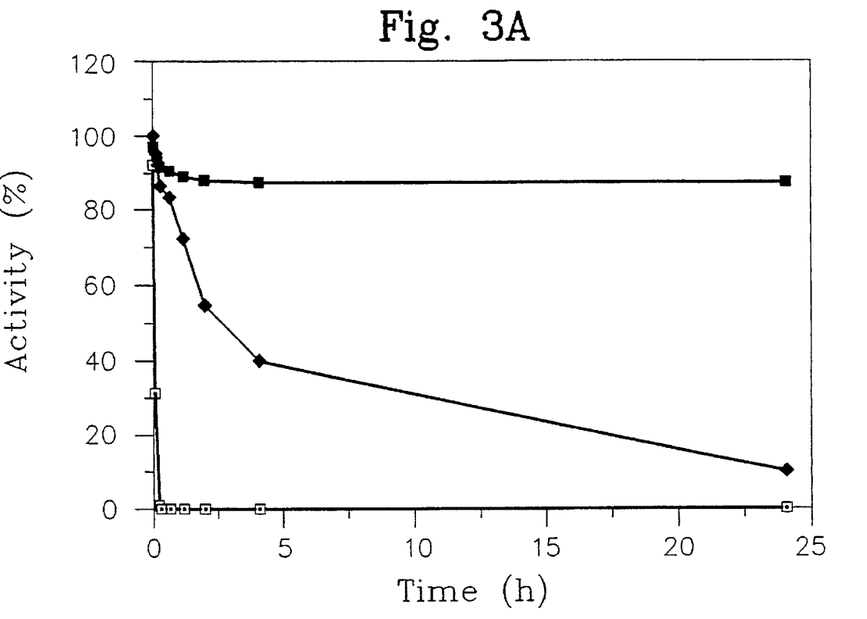
Figure 3B:
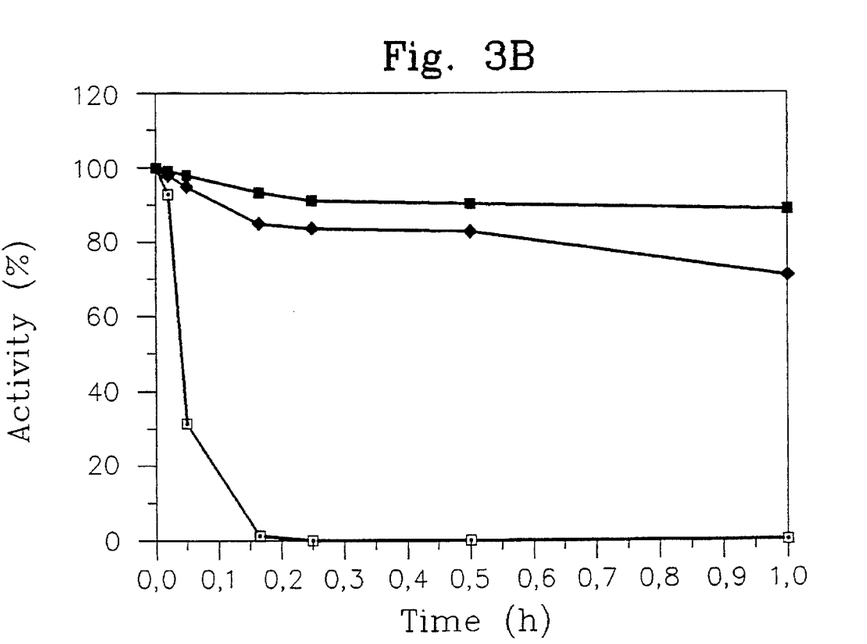

The pullulanase has a residual activity after 24 hours of incubation at 70° C. and pH 6.0, of more than 60% relative, preferably more than 80% relative, as shown in FIG. 3A. As shown in FIG. 3B, the pullulanase has a residual activity after 1 hour of incubation at 80° C. and pH 6.0, of more than 40% relative, preferably more than 60% relative.

Pullulan is degraded endoglycolytically and cleaved only at its α-1,6-linkages by the pullulanase of the invention. The action pattern of the pullulanase is typical of random endo-attack. Starch and amylose are almost unattacked by the pullulanase.

Immunochemical Properties

The pullulanase of the invention has immunochemical properties identical or partially identical to those of the pullulanases derived from Fervido-bacterium sp. Ven 5, DSM 6204.

The immunochemical properties can be determined by immunological cross-reaction identity tests. The identity tests can be performed by the well-known Ouchterlony double immunodiffusion procedure or by tandem crossed immuno-electrophoresis according to Axelsen N. H.; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum is generated, according to the above mentioned method, by immunizing rabbits with the purified pullulanase of the invention. The immunogen is mixed with Freund's adjuvant and injected subcutaneously into rabbits every second week. Antiserum is obtained after a total immu-nization period of 8 weeks, and immunoglobulin is prepared therefrom as described by Axelsen N. H., supra.

Preparation of the Pullulanase

The pullulanases of the invention can be prepared by cultivation of a pullulanase producing strain of Thermotogales in a suitable nutrient medium to containing carbon and nitrogen sources and inorganic salts followed by recovery of the desired enzyme, by methods known in the art per se.

Preferably, the pullulanases are prepared by cultivation of a pullulanase producing strain of Fervidobacterium, more preferred the strain Fervidobacterium sp. Ven 5, or a mutant or a variant thereof.

Alternatively, the pullulanase may be produced by recombinant DNA technology by methods known in the art per se, e.g. isolating a DNA fragment encoding the pullulanase, combining the DNA fragment with an appropriate expression signal in an appropriate plasmid vector, introducing the plasmid vector into an appropriate host (i.e. an *Escherichia coli*, or a member of the genus Bacillus, e.g. *B. lentus, B. subtilis, B. licheniformis,* and *B. amyloliquefaciens,* Aspergillus, or Streptomyces), either as an autonomously replicating plasmid or integrated into the chromosome, cultivating the host organism under conditions leading to expression of the pullulanase, and recovering the pullulanase from the culture medium.

The DNA fragment encoding the pullulanase may be isolated from a strain of Fervidobacterium, preferably the strain Fervidobacterium sp. Ven 5, DSM 6204, or a mutant or a variant thereof.

Preferably, the host organism is an *Escherichia coli*, or a member of the genus Bacillus, Aspergillus, or Streptomyces.

In a more specific embodiment, the plasmid is pSJ933, pBR322, or pACYC177, or a derivative hereof, and the host organism is *E. coli*.

In another specific embodiment, the plasmid is pUB110, pE195, pAMβ1, or pC194, or a derivative hereof, and the host organism is a Bacillus sp., preferably *B. subtilis, B. licheniformis, B. amyloliquefaciens* or *B. lentus*.

Starch Converting Processes

Being a debranching enzyme, having an excellent thermostability and substrate specificity, the pullulanase of the invention is valuable for use in starch converting processes. The pullulanase of the invention may be used together with a saccharifying enzyme for saccharification of liquefied starch into glucose or maltose.

Saccharification processes can be carried out by conventional means and essentially as described in e.g. U.S. Pat. No. 3,912,590, EP Patent Publications Nos. 252,730 and 63,909, and International Patent Application WO 90/11352. Preferred enzyme dosages are in the range of 1–100 μg of pullulanase per g dry substance, more preferred 1–50 μg/g dry substance. Suitable saccharifying conditions are at pH 4.5–7 and at 55°–70° C.

The invention is further illustrated in the following examples, which are not intended to be in any way limiting to the scope of the invention as claimed.

EXAMPLE 1

Cultivation Example

The strain DSM 6204 was cultivated at 60° C. under continuous gassing with $N_2/CO_2$ (80:20) in a medium (starch complex medium) of the following composition (per liter):

| | |
|---|---|
| $K_2HPO_4$ | 1.6 g |
| $NaH_2PO_4 \times 2 H_2O$ | 1.0 g |
| $(NH_4)_2SO_4$ | 0.8 g |
| $NH_4Cl$ | 0.6 g |
| Tryptone | 1.0 g |
| Yeast extract | 1.0 g |
| Peptone | 1.0 g |
| $MgSO_4 \times 7H_2O$ | 0.4 g |
| $CaCl_2 \times 2H_2O$ | 0.2 g |
| Trace Element Solution SL 11 | 1.0 ml |
| Vitamine Solution* (10-fold) | 2.0 ml |
| Soluble starch** | 2.5 g |
| Resazurin | 1.0 mg |
| $Na_2S \times 9 H_2O$ | 0.5 g |
| $NaHCO_3$ | 1.0 g |
| Water ad 1000 ml | |
| pH: 6.8–7.0 | |

*Vitamin solution according to WOLIN et al., 1964, J. Bacteriol. 87, p. 993–998.
**Soluble starch from Fluka The medium was prepared anaerobically under $N_2/CO_2$ (80:20). $CaCl_2;2H_2O$, $Na_2S;9H_2O$ and $NaHCO_3$ were autoclaved separately under nitrogen. The $Na_2S$-solution was adjusted to pH 7.0 before it was added to the medium.

During growth amylolytic and pullulytic activity, optical density, pH, and residual starch concentration were measured. After 20 hours of growth 20 U/l amylase and 20 U/l pullulanase were detected in the cell free supernatant.

Method of Analysis for Pullulanase Activity

Pullulanase activity was measured by determining the amount of reducing sugars liberated during incubation with pullulan at 85° C. and pH 6.0. The activity of 1 U of pullulanase was defined as that amount of enzyme which liberates 1 μmol of reducing sugar per minute using maltose as a standard. The enzymatic reactions were conducted in 50 mM sodium-phosphate buffer, pH 6.0, the concentration of the substrate was 0.5% (w/v).

The reaction mixture was prepared by adding 50 μl enzyme solution to 200 μl substrate solution. The mixture was incubated at 85° C. for 5 minutes, cooled and diluted with 2.5 ml water. After incubation 250 μl dinitrosalicylic acid reagent (i.e. dinitrosalicylic acid 1 g, 2 N NaOh 20 ml, K-Na-tartratex4 H$_2$O 30 g, and distilled water 100 ml) were added. The optical density was measured at 546 nm against a mixture which was not incubated.

The activity of the enzyme solutions which were used in the various incubations was:

| | |
|---|---|
| 1) Temperature optimum (FIG. 1A) | 1.2 U/ml |
| 2) pH optimum (FIG. 1B) | 1.8 U/ml |
| 3) Degradation of pullulan, branched oligosaccharides and amylose (FIG. 2) | 0.25 U/ml |
| 4) Initial activity of the pullulanase solution used for the investigation of the thermal stability (FIGS. 3–4) | 6.5 U/ml |
| 5) Activity of pullulanase against various glucose polymers (Table 2) | 2.5 U/ml |
| 6) Influence of metal ions, cyclodextrins and glucose polymers on the activity of the pullulanase (Table 3) | 1.0 U/ml |
| The concentration of inhibitors was: | |
| Metal ions and cyclodextrins | 5 mM |
| Glucose polymers | 0.05% |

EXAMPLE 2

Purification Example 40 l of cell free supernatant obtained according to Ex. 1 were concentrated 200 fold, dialysed against 50 mM sodium phosphate pH 7.5, and separated by ionexchange chromatography with Q-Sepharose. Pullulanase did not bind to the column but was eluted during washing with buffer.

The fractions containing pullulytic activity were pooled, concentrated and separated by gel filtration on a Hi Load 16/60 Supadex 200 column. After this procedure the pullulanase was free of amylase and only very low amylolytic activity which was due to unspecific reactions of the pullulanase could be detected.

Further purification was achieved by hydrophobic chromatography on Phenyl-Superose with a decreasing (NH$_4$)$_2$SO$_4$-gradient (1.5M–)M).

The recovery of pullulanase during purification is presented in Table 1 below.

TABLE 1

| Recovery of Pullulanase during Purification | | | | |
|---|---|---|---|---|
| Step | Total protein (mg) | Total activity (units) | Specific activity (units/mg) | Recovery (%) |
| Concentration | 130 | 226 | 1.7 | 100 |
| Ion-exchange chromatography on Q-Sepharose | 13.3 | 226 | 16.9 | 100 |
| Gelfiltration with Supadex 200 | 2.7 | 176.4 | 65.3 | 78 |
| Hydrophobic chromatography on Phenyl- | 0.45 | 49.4 | 109.7 | 22 |

TABLE 1-continued

| Recovery of Pullulanase during Purification | | | | |
|---|---|---|---|---|
| Step | Total protein (mg) | Total activity (units) | Specific activity (units/mg) | Recovery (%) |
| Suparose | | | | |

After this procedure the specific activity of the pullulanase reached approximately 110 U/mg and most of the experiments were performed with enzyme which was purified in the above mentioned manner.

The enzyme purified to homogeneity by preparative gel electrophoresis and SDS-gel electrophoresis reveealed only one protein band with a molecular mass of 78,000 Da. Due to the low stability of the pullulanase during this separation the specific activity decreased to 8 U/mg.

EXAMPLE 3

Characterization Example

The purified pullulanase obtained according to Ex. 2 was subjected to characterization using the method for analyzing pullulanase activity described in Ex. 1.

pH and Temperature Optima

As presented in FIG. 1A, the pullulanase is active at temperatures from below 45° C. to above 100° C., having its temperature optimum in the range of from 75°–90° C., more preferred in the range 80°–90° C., around 85° C. (at pH 6.0).

As presented in FIG. 1B, the pullulanase is active of from pH approx. 3.5 to pH above 8, having a rather broad pH optimum in the range of from ph 4.5 to pH above 8, more preferred in the range pH 5–7 (at 85° C.).

Substrate Specifity

The pullulanase was incubated with different glucose polymers such as starch, pullulan, branched oligosaccharides, amylose and glycogen.

As shown in Table 2 below, the enzyme showed the highest activity with pullulan as a substrate and 50% of the pullulytic activity were detected if it was incubated with branched oligosaccharides. Starch and amylose remained almost unattacked, only 5–10% of the pullulytic activity were found with these substrates. The highly branched saccharide glycogen was not degraded.

TABLE 2

| Pullulanase Activity on Various Glucose Polymers | |
|---|---|
| Substrate | Activity (%) |
| Pullulan | 100 |
| Branched oligosaccharides | 41 |
| Starch | 7 |
| Amylose | 4 |
| Glycogen | 0 |

All substrates were used in a concentration of 0.5%.

Figure 2A:
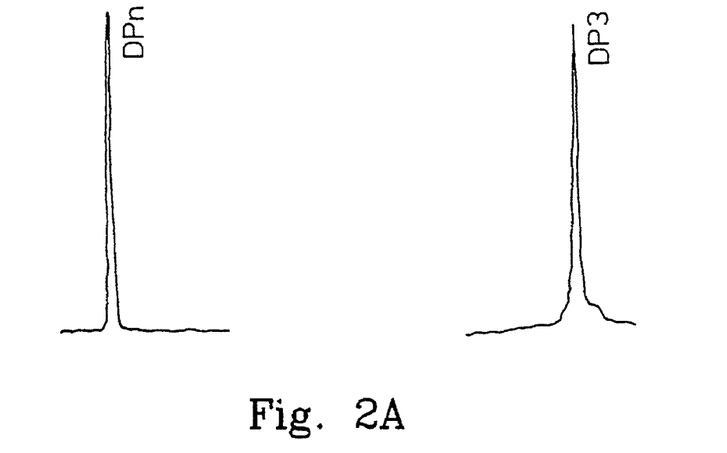
Figure 2B:
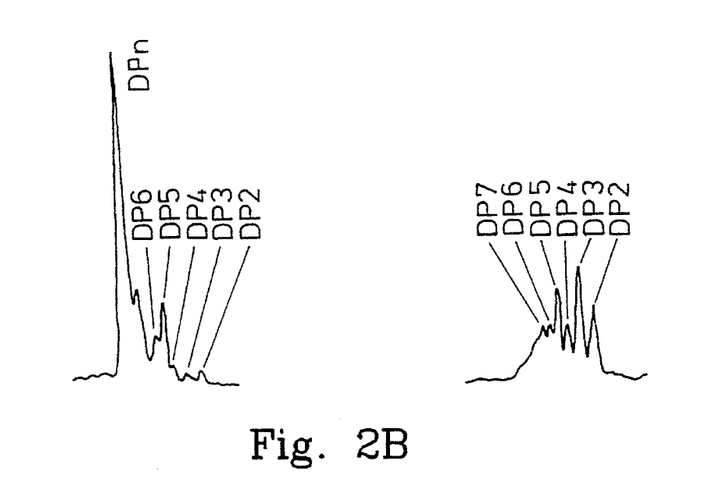
Figure 2C:
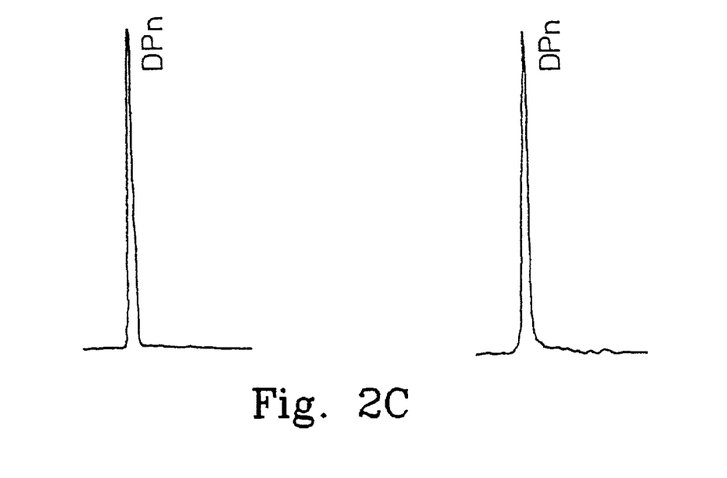

Analysis of the sugars released during the degradation of pullulan, branched oligosaccharides and amylose showed that pullulan was degraded endoglycolytically and cleaved only at its α-1,6-linkages (as presented in FIG. 2). Also the branched oligosaccharides were attacked only on their branching points, and the released linear oligomers were easily degraded by an added α-glucosidase to glucose. Amylose remained almost unattacked.

Influence of Metal Ions, Cyclodextrins and Glucose Polymers on the Pullulytic Activity To investigate the influence of metal ions, cyclodextrins and various glucose polymers on the activity of the pullulanase the purified enzyme was incubated with a 0.5% pullulan solution (pH 6.0) in the presence of up to 5 mM of metal ions and cyclodextrins. Amylose, starch, glycogen, pullulan and branched oligosaccharides were added in concentrations of up to 0.05%.

As shown in Table 3 below, calcium, magnesium, molybdenum ions and EDTA did not influence the pullulytic activity. The addition of cobalt and nickel ions as well as α-cyclodextrins decreased the activity of the enzyme slightly and in the presence of 5 mM of copper, zinc, and chromate ions or β-cyclodextrin the pullulanase was inhibited completely.

Surprisingly, the addition of amylose and starch did also influence the pullulanase and about 20 to 30% of the initial activity were found if 0.05% of this polymer was added.

TABLE 3

Influence of Metal Ions, Cyclodextrins and Glucose Polymers on Pullulanase Activity

| Inhibitor | Activity (%) |
|---|---|
| None | 100 |
| $CuSO_4$ | 0 |
| $ZnSO_4$ | 8 |
| $COCl_2$ | 57 |
| $NiCl_2$ | 35 |
| $KCr(SO_4)_2$ | 10 |
| $CaCl_2$ | 100 |
| $MgSO_4$ | 100 |
| $NaMoO_4$ | 100 |
| EDTA | 100 |
| α-Cyclodextrin | 57 |
| β-Cyclodextrin | 4 |
| Starch | 33 |
| Amylose | 22 |
| Branched Oligosaccharides | 100 |
| Glycogen | 100 |
| Pullulan | 100 |

Values represent the pullulytic activity in the presence of 5 mM metal ions of 0.05% of glucose polymer.
1.0 U/ml of pullulanase activity was used throughout incubation.

Thermal Stability

Investigation of the thermal stability showed that the enzyme could be incubated in the absence of substrate and metal ions at 70° C. for 24 hours at a pH of 6.0 without any substantial loss of activity (vide FIG. 3A (■)).

During incubation at 80° C. only approximately 10% of the initial activity could be detected after the same period (vide FIG. 3A (567 )). At 90° C. the enzyme was inactivated within 15 minutes (vide FIG. 3B (□)).

Figure 4A:
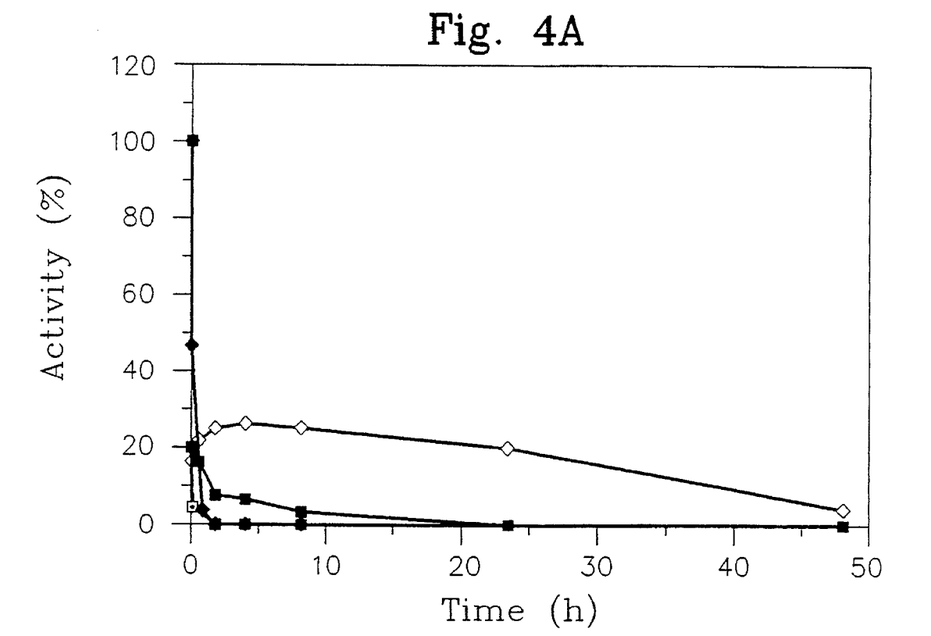
Figure 4B:
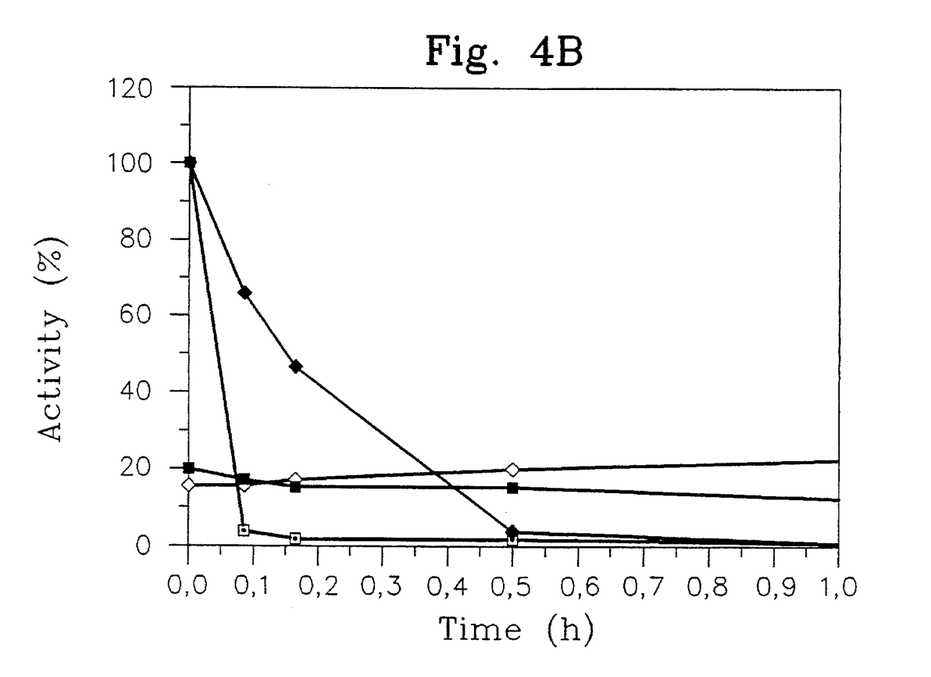

In order to investigate the thermal stability under the conditions prevailing in the starch saccharification process the enzyme was also incubated in the presence of starch and calcium ions at 80° C. and pH 4.5 (vide FIG. 4).

Both the addition of calcium ions and starch increased the thermal stability significantly although the activity of the pure enzyme was reduced. In the absence of starch and metal ions the enzyme was completely inactivated during 10 minutes of incubation. In the presence of 5 mM calcium the inactivation was slower, 5% of the initial activity were detected after 30 min. The addition of starch increased the thermal stability significantly although the initial pullulytic activity was reduced to 20% of the starch free sample.

The highest stability was observed in the presence of both calcium ions and starch. Under these conditions the pullulanase was stable for 24 hours.

EXAMPLE 4

Cloning of a Pullulanase Gene from Fervidobacterium

Fervidobacterium sp. Ven 5 (DSM 6204) chromosomal DNA was isolated according to Pitcher et al. (1989); Lett. Appl. Microbiol., 8, 151–156) and partially digested with Sau3A. 100 μg of Fervidobacterium DNA were digested with 20 units of Sau3A for 10 min. at 37° C. The digestion was terminated by phenol:chloroform extraction and the DNA was ethanol precipitated.

Figure 5:
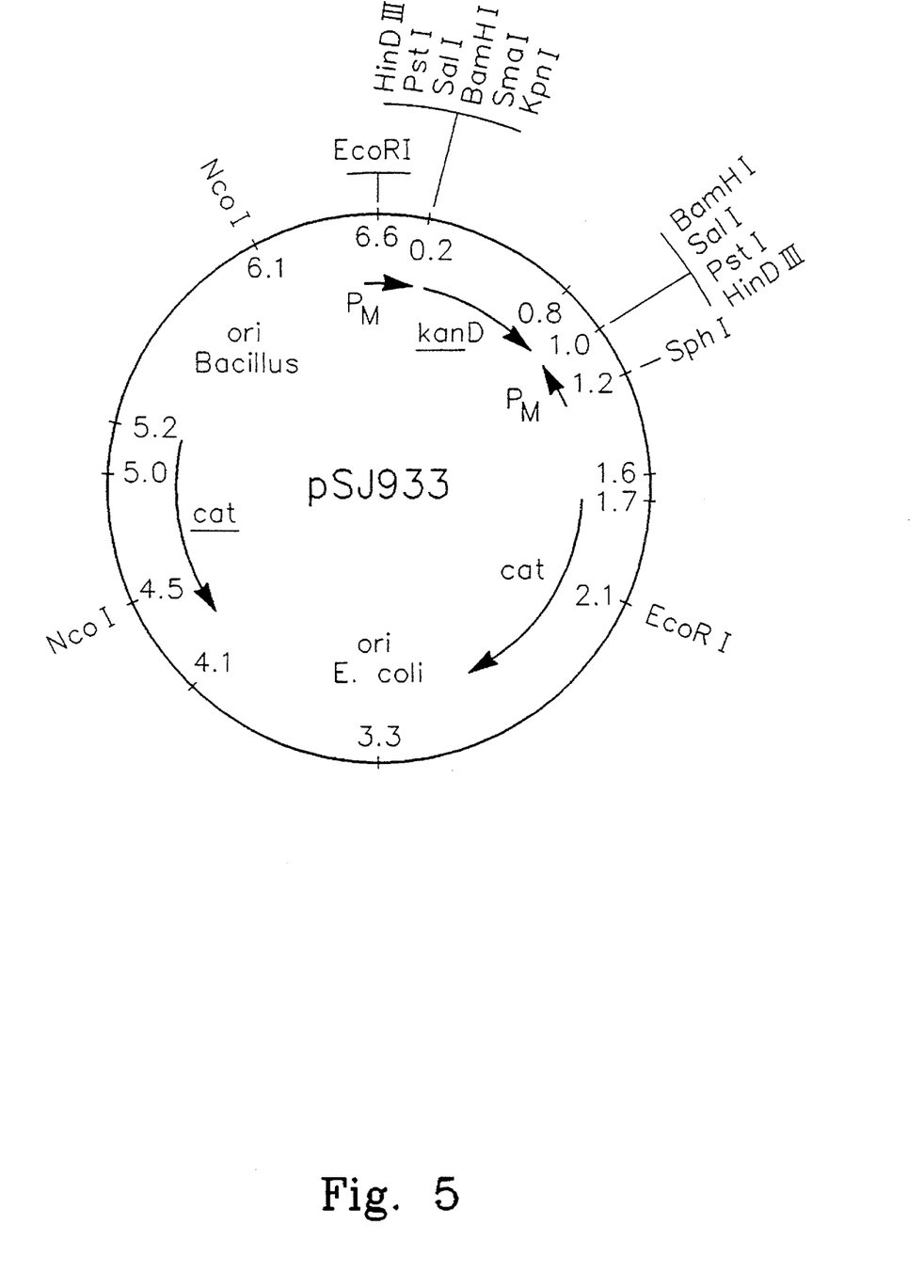
FIG. 5 shows a restriction map of plasmid pSJ933, deposited on 26 Sep. 1990 in *E. coil* strain SJ989 at NCIMB No. 40320.

Ligation was performed by using chromosomal DNA: pSJ933 (Digested by BamHI and the larger fragment of 5.8 kb was isolated) with a ratio of 1:3 using 4 μg of DNA/10 μl and adding 2 units of T4 ligase and incubating at room temperature (25° C.) for 4 hours. The plasmid pSJ933 has been deposited in the E. coil strain SJ989 on 26 Sep. 1990 according to the Budapest Treaty at National Collections of Industrial & Marine Bacteria Ltd., 23 St. Machar Drive, Aberdeen AB2 1RY, Scotland, UK, under Accession No. NCIMB 40320. A restriction map of the plasmid is shown in FIG. 5.

E. coli strain MC1000 was transformed with the ligated DNA and plated on Luria broth plus 2% agar containing 10 μg/ml chloramphenicol and incubated at 37° C. After 16 hours of incubation approximately 14,000 chloramphenicol resistant colonies were observed on the plates. These colonies were replica plated onto a new set of Luria broth plates containing 2% agar, 6 μg/ml chloramphenicol and 0,1% dyed pullulan and grown overnight.

(Dyed pullulan: 50 g pullulan (Hayashibara Biochemical laboratories) and 5 g of Cibachrom Rot B (Ciba Geigy) are suspended in 500 ml 0.5M NaOH) and the mixture is incubated under constant stirring at room temperature for 16 hours. pH is adjusted to 7.0 with 4N $H_2SO_4$. The dyed pullulan is thereafter harvested by centrifugation and the pullulan is washed 3 times with distilled water and resuspended in an appropriate volume of distilled water).

The plates were then incubated at 60° C. for 4 hours and around one of the colonies a halo appeared resulting from degradation of the dyed pullulan. The corresponding colony on the first set of Luria broth plates was isolated and analyzed for plasmid content.

The isolated colony PL2125 was grown in 10 ml Luria broth, the plasmid was isolated by the method described by Kieser et al.; Plasmid 12:19 (1984). The plasmid was analyzed by restriction mapping and showed an insert of Fervidobacterium DNA of approximately 4.5 kb.

EXAMPLE 5

Pullulan Hydrolysis

The following experiments were performed on a pullulanase sample obtained according to Ex. 2, and compared to a commercially available Bacillus pullulanase preparation (Promozyme™, Novo Nordisk NS Denmark).

Pullulan is a linear D-glucose polymer consisting essentially of maltotriosyl units joined by 1,6-alpha links.

Endo-pullulanases hydrolyse the 1,6-alpha links at random, and the number of links hydrolysed was determined as reducing carbohydrate using a modified Somogyi-Nelson method.

One pullulanase unit (PUN) is defined as the amount of enzyme which, under standard conditions (i.e. 40° C.; pH 5.0; 30 minutes reaction time; and with 0.2% pullulan as substrate) hydrolyses pullulan, liberating reducing carbohydrate with a reducing power equivalent to 1 μmol glucose per minute. A folder AF 190/2 describing this analytical method is available upon request to Novo Nordisk NS, Denmark, which folder is hereby included by reference.

Pullulan Hydrolysis

Pullulan substrates were prepared by dissolving 5.0 g of pullulan (HAYASHIBARA PSS20818) in 100 ml 0.05 ml 0.05M, pH 5.0 citrate buffer. The hydrolysis reactions were carried out in 50 ml flasks, fitted with a screw-cap, placed in a shaking water bath at 50° C.

The enzyme was dosed on basis of dry substance (DS), 1 PUN/g DS, and the following results were obtained from the HPLC analysis (DP, degree of polymerization):

| Enzyme | Reaction time (hours) | % DP1 | % DP2 | % DP3 | % DP4+ |
|---|---|---|---|---|---|
| Promozyme | 1 | — | — | 7.0 | 93.0 |
| (1 PUN/g DS) | 2 | — | — | 7.9 | 92.1 |
| | 4 | — | — | 10.1 | 89.9 |
| | 6 | — | — | 11.9 | 88.1 |
| | 24 | 0.3 | — | 17.8 | 82.0 |
| | 48 | 0.5 | — | 18.0 | 81.5 |
| | 1 | — | — | 12.4 | 87.6 |
| | 2 | — | — | 12.8 | 87.2 |
| Fervidobacterium | 4 | — | — | 17.2 | 82.8 |
| pullulanase | 6 | — | — | 21.3 | 78.7 |
| (1 PUN/g DS) | 24 | 0.5 | — | 57.4 | 42.1 |
| | 48 | 0.9 | — | 76.2 | 22.9 |

Figure 6:
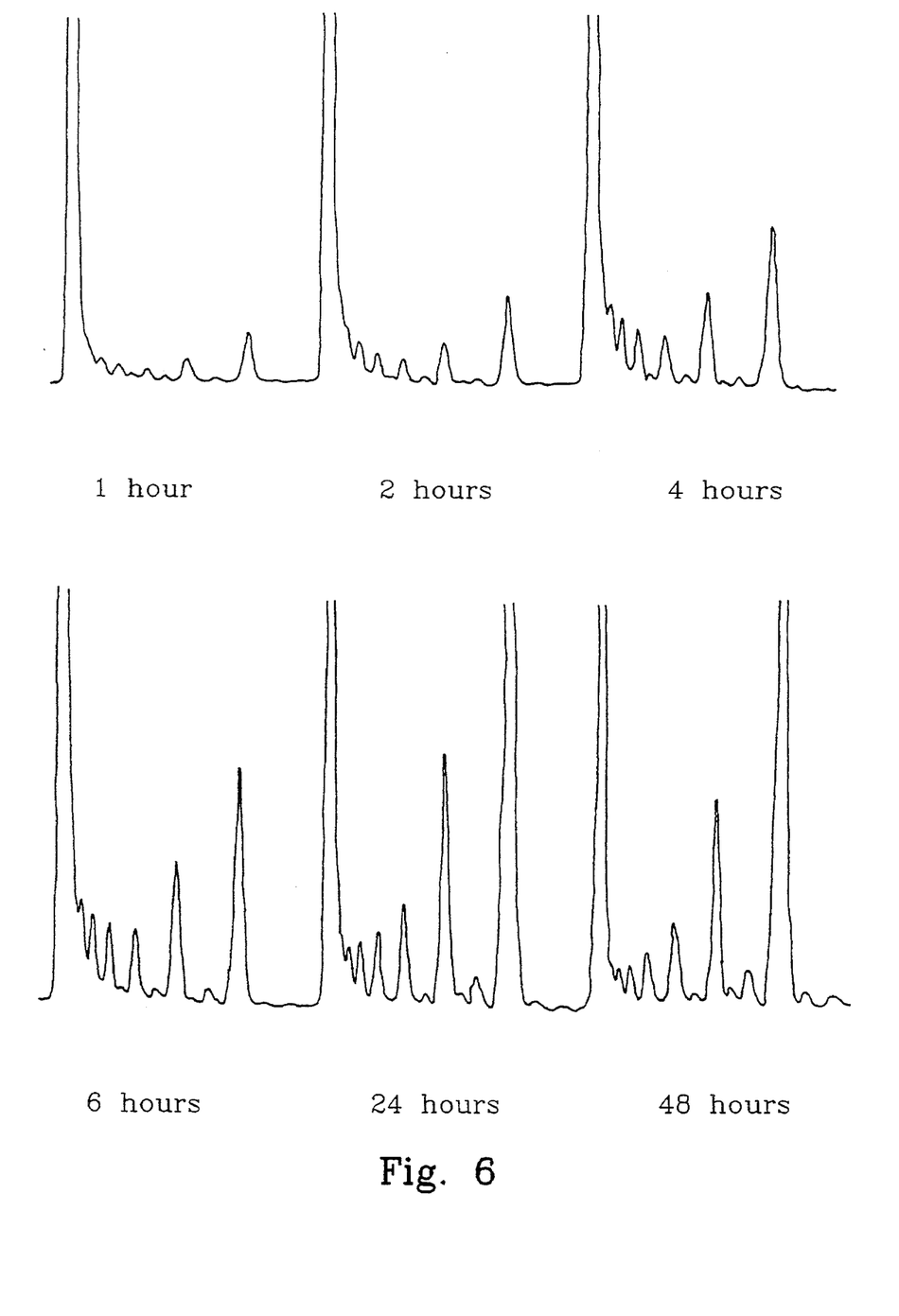
FIGS. 6–7 show chromatograms obtained after 1, 2, 4, 6, 24, and 48 hours of incubation, from the hydrolysis of pullulan by a pullulanase of the invention (FIG. 6) and a Bacillus pullulanase (Promozyme™, FIG. 7), respectively.
Figure 7:
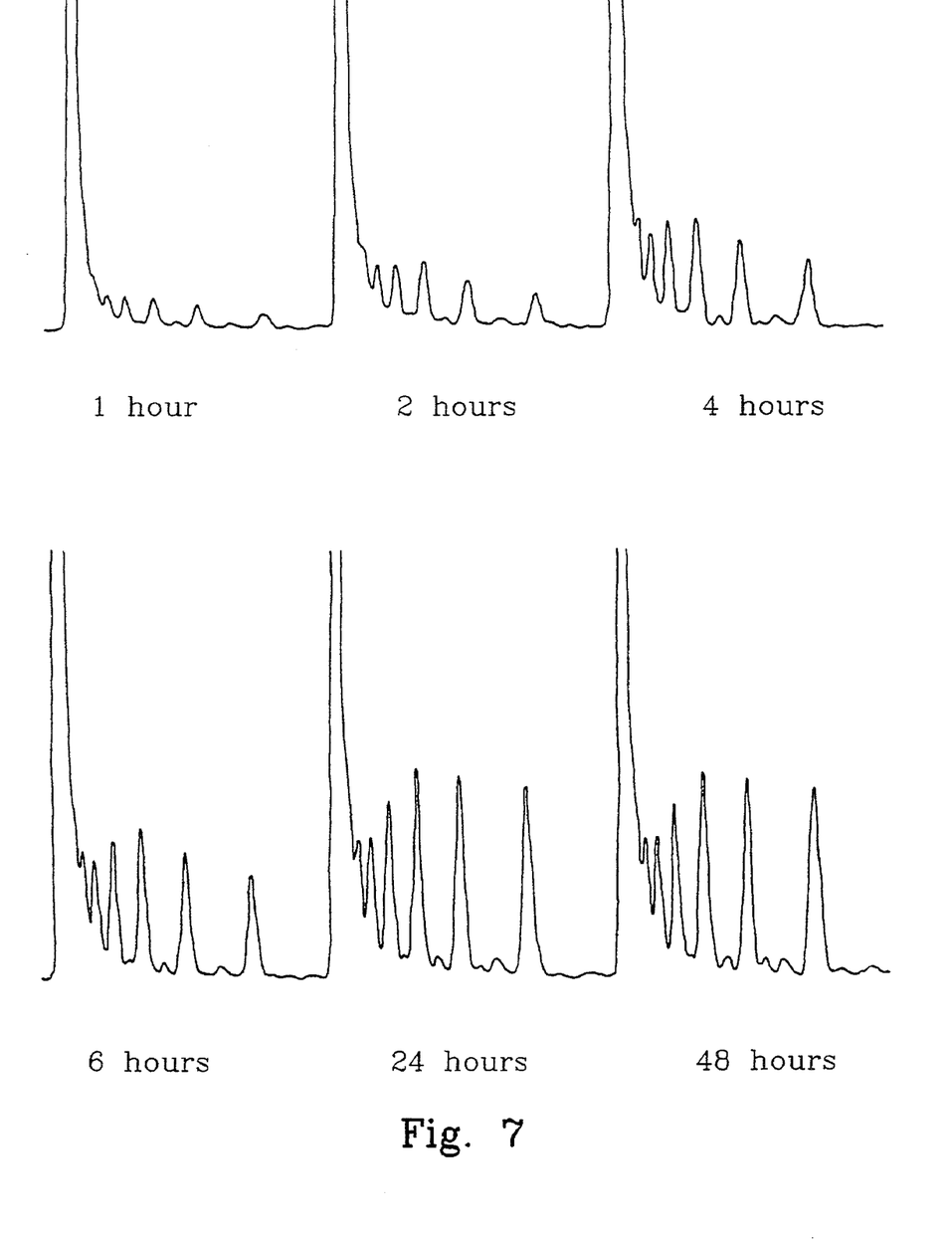

The samples were also submitted for GPC analysis. The chromatograms obtained are presented in FIGS. 6–7.

During the initial stages of hydrolysis, maltotriose and a series of 1,6-alpha-linked oligomers of maltotriose were formed. The action pattern was typical of random endo-attack. Proportionally more maltotriose was generated with the enzyme of the invention.

We claim:

1. An isolated pullulanase endogenous to the strain Fervidobacterium sp. Ven 5, DSM 6204, or a mutant thereof which is capable of producing the pullulanase having:

(a) a temperature optimum in the range 80°–90° C.;

(b) a pH optimum in the range of 5–7; and (c) at least 60% residual activity after 24 hours of incubation at pH 6.0.

2. The pullulanase according to claim 1 which has at least 80% residual activity after 24 hours of incubation at pH 6.0.

3. The pullulanase according to claim 2 which is derived from the strain Fervidobacterium sp. Ven 5, DSM 6204.

4. A method for producing the pullulanase according to claim 1, comprising:

(a) isolating a DNA fragment from the strain encoding the pullulanase;

(b) placing the DNA fragment with host-specific transcriptional and translational regulatory DNA sequence elements in an appropriate plasmid vector;

(c) introducing the plasmid vector into an appropriate host organism either as an autonomously replicating plasmid or integrated into the chromosome;

(d) cultivating the host organism under aerobic conditions suitable for expression of the pullulanase; and (e) recovering the pullulanase from the culture medium.

5. The process according to claim 4, wherein the host organism is selected from the group consisting of *Escherichia coli*, Bacillus, Aspergillus and Streptomyces.

6. The process according to claim 5, wherein the host organism is *Escherichia coli* and the plasmid vector is selected from the group consisting of pSJ933, NCIMB 40320, pBR322, and pACYC177, or a derivative hereof.

7. The process according to claim 5, wherein the host organism is a Bacillus sp. and the plasmid is selected from the group consisting of pUB110, pE195, pAMβ1, or pC194, or a derivative hereof.

8. The process according to claim 5, wherein the host organism is selected from the group consisting of *B. subtilis, B. licheniformis, B. amyloliquefaciens* and *B. lentus*.

* * * * *